(12) United States Patent
Dillard

(10) Patent No.: US 10,207,091 B2
(45) Date of Patent: Feb. 19, 2019

(54) FORCE-DIRECTIONAL NASAL SURGERY DILATATION DEVICE

(71) Applicant: David G. Dillard, Atlanta, GA (US)

(72) Inventor: David G. Dillard, Atlanta, GA (US)

( * ) Notice: Subject to any disclaimer, the term of this patent is extended or adjusted under 35 U.S.C. 154(b) by 1100 days.

(21) Appl. No.: 14/484,480

(22) Filed: Sep. 12, 2014

(65) Prior Publication Data

US 2015/0080935 A1    Mar. 19, 2015

Related U.S. Application Data

(60) Provisional application No. 61/877,473, filed on Sep. 13, 2013.

(51) Int. Cl.
*A61M 25/10* (2013.01)
*A61M 29/02* (2006.01)
*A61B 17/24* (2006.01)

(52) U.S. Cl.
CPC .............. *A61M 29/02* (2013.01); *A61B 17/24* (2013.01); *A61M 25/1002* (2013.01); *A61M 2025/1084* (2013.01)

(58) Field of Classification Search
CPC .... A61B 17/24; A61M 25/1002; A61M 29/02
USPC ....... 606/159, 190, 191, 192, 193, 194, 195, 606/196
See application file for complete search history.

(56) References Cited

U.S. PATENT DOCUMENTS

| | | | |
|---|---|---|---|
| 3,800,788 A | 4/1974 | White | |
| 4,606,346 A * | 8/1986 | Berg | A61F 5/34 |
| | | | 606/196 |
| 5,071,406 A | 12/1991 | Jang | |
| 5,139,510 A * | 8/1992 | Goldsmith, III | A61B 17/12104 |
| | | | 604/907 |
| 5,624,395 A | 4/1997 | Mikhail et al. | |
| 5,645,529 A | 7/1997 | Fagan et al. | |
| 6,391,002 B1 | 5/2002 | Kokish | |

(Continued)

FOREIGN PATENT DOCUMENTS

EP    0624349 A1    11/1994

OTHER PUBLICATIONS

P. Bartra et al., Balloon catheter technology in rhinology: Reviewing the Evidence, Sep. 7, 2010, 226-232, vol. 121(1), The American Laryngological, Rhinological, and Otological Society, Inc.

*Primary Examiner* — Vy Bui
(74) *Attorney, Agent, or Firm* — Morris, Manning & Martin, LLP; John R. Harris

(57) ABSTRACT

A force-directional nasal surgery dilatation device for use in a medical procedure such as sinuplasty, correction of deviated septum, and expansion of sinus cavities and nasal passages. An inflatable balloon is affixed to the distal end of a shaft for supporting and guiding the balloon into position for a nasal surgery procedure involving a patient. The shaft includes an inflation passageway associated for introducing an inflation medium into the balloon. The device further includes a force distribution member affixed to the inflatable balloon that provides a relatively rigid surface for applying distributed force against a tissue in the patient's nasal cavity upon inflation of the balloon. The force distribution member can include a pair of generally planar articulated adjacent surfaces attached along a hinge line between the surfaces.

9 Claims, 24 Drawing Sheets

(56) References Cited

U.S. PATENT DOCUMENTS

| | | |
|---|---|---|
| 7,491,188 B2 | 2/2009 | Holman et al. |
| 7,645,272 B2 | 1/2010 | Chang et al. |
| 7,654,997 B2 | 2/2010 | Makower et al. |
| 7,803,150 B2 | 9/2010 | Chang et al. |
| 8,303,640 B2 | 11/2012 | Hepworth et al. |
| 2013/0116655 A1 | 5/2013 | Bacino et al. |
| 2013/0184683 A1 | 7/2013 | Chow et al. |

* cited by examiner

FORCE-DIRECTIONAL NASAL SURGERY DILATATION DEVICE

CROSS-REFERENCE TO RELATED APPLICATION

This application claims the benefit of Provisional U.S. Patent Application Ser. No. 61/877,473, filed on Sep. 13, 2013, which application is incorporated by reference herein in its entirety.

TECHNICAL FIELD

The present invention relates, in general, to medical devices, and, in particular, to medical devices and related methods for the treatment of sinus conditions.

BACKGROUND

Balloon dilatation devices have been used to treat constricted paranasal sinus passageways for several years. These balloon dilatation devices generally involve the use of an inflatable balloon located at the distal end of a catheter such as a balloon catheter. The balloon catheter may include a substantially rigid inner guide member and a movable shaft coupled to a balloon that is slidably mounted on the rigid inner guide member. The inner guide member might be a stainless steel wire or flexible plastic member to facilitate the location and access of sinus ostia, and is generally introduced through the nostril into the target sinus under endoscopic visualization. A flexible wire or flexible plastic member is introduced through the inner guide member and gently advanced into the target sinus. The balloon catheter generally slides over the inner guide member and the flexible wire, and it is positioned across the constricted ostium. The balloon is gradually inflated, generally with a liquid medium, to gently restructure the constricted ostium. The balloon is then deflated and removed, and an irrigation system may be advanced to wash the sinus with a sterile solution. Generally, this procedure is referred to as Balloon Sinuplasty™, and a number of U.S. patents and patent applications including U.S. Pat. Nos. 7,645,272, 7,654,997, and 7,803,150 describe various embodiments of the medical procedure and devices used in the performance of such procedure.

Such conventional methods and apparatus, however, have significant drawbacks. Generally, these methods do not provide a way to advance the inner guide member and balloon catheter easily and effectively, especially in patients with constricted nostrils or deviated septums or constricted openings to the middle meatus. Additionally, traditional balloon catheters distribute the force equally on the surrounding structures during the dilatation process. In some cases, the balloon catheter is located near critical structures that can be easily damaged by the omnidirectional force applied by traditional balloon catheters. Therefore, there has been a long-desired but unresolved need for a system or method that could direct the force applied by a balloon catheter during the dilatation process for protecting delicate structures and also for aiding in the process of accessing the target paranasal sinus.

SUMMARY

According to a first embodiment, a force-directional nasal surgery dilatation device for use in a nasal surgery is provided, the device comprising:

an inflatable balloon;

a shaft for supporting the balloon at a distal end and guiding the balloon into position for a procedure involving a patient;

an inflation passageway associated with the shaft for introducing an inflation medium into the balloon; and a force directional member adjacent a side of the balloon;

wherein, when the balloon is inflated in a nasal passage or sinus ostia of the patient, the amount of force applied to tissue adjacent the force directional member is less than the amount of force applied to other tissue in the nasal passage or sinus ostia of the patient.

According to a second embodiment, a method for the dilatation of a nasal passage or sinus ostia of a patient is provided, the method comprising:

advancing the distal end of a device as set forth above into a nasal passage or sinus ostia of the patient such that the balloon is positioned in an area to be treated;

inflating the balloon within the nasal passage or sinus ostia to apply pressure to tissue adjacent the balloon;

deflating the balloon;

removing the device from the patient.

According to a third embodiment, a force-directional nasal surgery dilatation device for use in a nasal surgery is provided, the device comprising:

a shaft having a distal end and a proximal end, a distal axis adjacent the distal end and a proximal axis adjacent the proximal end, the shaft having an opening from the distal end to the proximal end to allow the passage of a balloon dilatation catheter therethrough; and a force directional member connected to the distal end of the shaft;

wherein the force directional member comprises: a proximal portion connected to the distal end of the shaft and projecting radially outward from the distal axis of the shaft and a central portion connected to the distal end of the proximal portion and extending along the distal axis of the shaft.

According to a fourth embodiment, a method for dilatation of a nasal passage or sinus ostia of a patient is provided, the method comprising:

advancing the distal end of the device of claim 16 into a nasal passage or sinus ostia of the patient such that the force directional member is positioned in an area to be treated;

advancing a balloon dilatation catheter comprising an inflatable balloon through the opening in the shaft until the balloon is adjacent the force directional member;

inflating the balloon within the nasal passage or sinus ostia to apply pressure to tissue adjacent the balloon;

deflating the balloon;

removing the balloon dilatation catheter and the device from the patient.

According to a fifth embodiment, a force-directional nasal surgery dilatation device for use in a nasal surgery is provided, the device comprising:

a shaft having a distal end and a proximal end, a distal axis adjacent the distal end and a proximal axis adjacent the proximal end, the shaft having an opening from the distal end to the proximal end to allow the passage of a balloon dilatation catheter therethrough;

an inflatable balloon, the inflatable balloon having a proximal end adjacent the distal end of the shaft and a distal end;

a force application member having a proximal end adjacent the distal end of the balloon and a distal end, wherein the force directional member is capable of forward linear movement relative to the shaft along the distal axis upon inflation of the inflatable balloon.

BRIEF DESCRIPTION OF THE DRAWINGS

The accompanying drawings illustrate one or more embodiments and/or aspects of the disclosure, and together with the written description, serve to explain the principles of the disclosure. Wherever possible, the same reference numbers are used throughout the drawings to refer to the same or like elements of an embodiment, and wherein:

FIGS. 1A-1E illustrate the use of a balloon dilatation device wherein: FIG. 1A shows the device with the balloon uninflated prior to insertion; FIG. 1B shows the device after insertion; FIG. 1C shows the inserted device with the balloon inflated; FIG. 1D shows the inserted device after the balloon has been deflated; and FIG. 1E shows the device after removal.

DETAILED DESCRIPTION

Figure 1A:
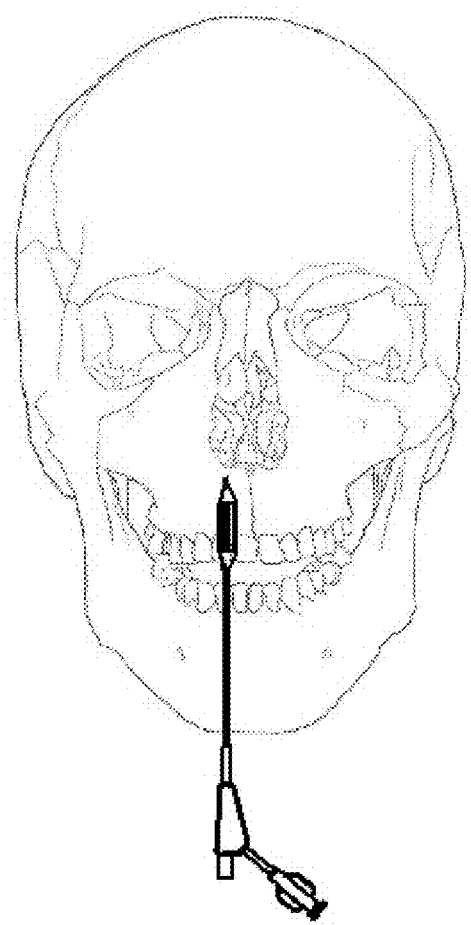

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates.

Figure 1B:
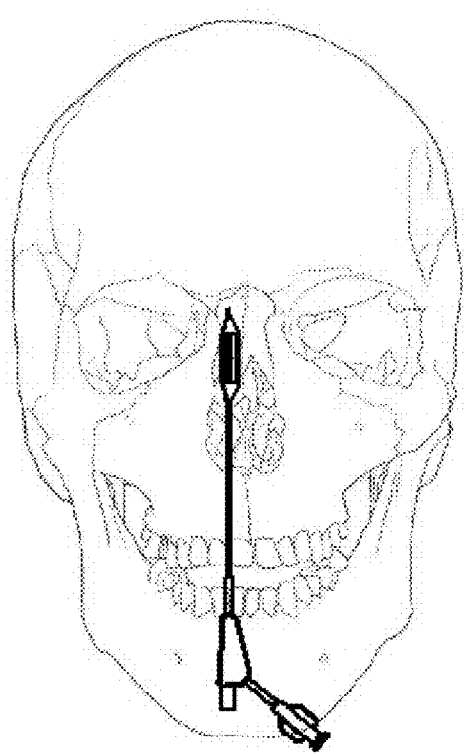
Figure 1C:
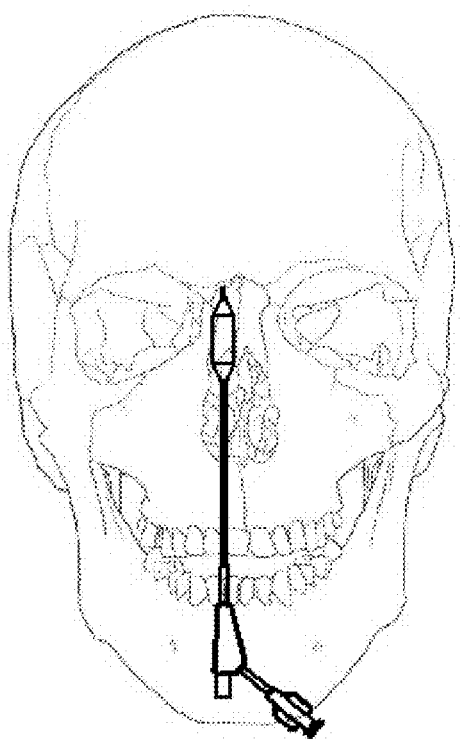
Figure 1D:
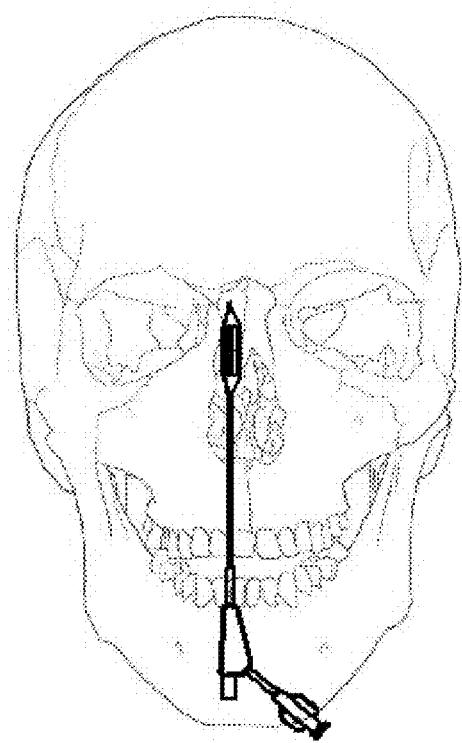
Figure 1E:
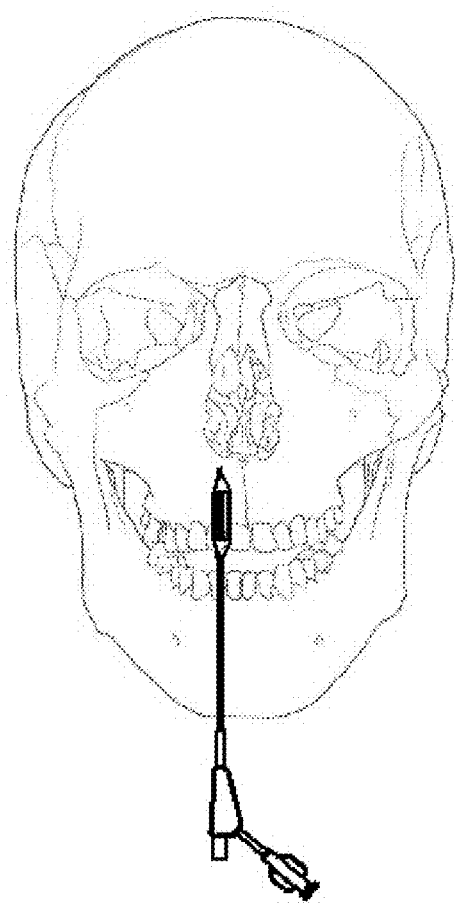

Referring now to the drawings, in which like numerals illustrate like elements throughout several drawing figures, FIGS. 1A-1E illustrate the use of a balloon dilatation device as described herein. FIG. 1A shows the device with the balloon uninflated prior to insertion. As shown in FIG. 1B, the device is advanced into the nasal passage or sinus ostia of a patient with the balloon deflated. When the balloon is adjacent the area to be treated, the balloon is then inflated as shown in FIG. 1C. The balloon is then deflated as shown in FIG. 1D and removed from the patient as disclosed in FIG. 1E.

Figure 2A:
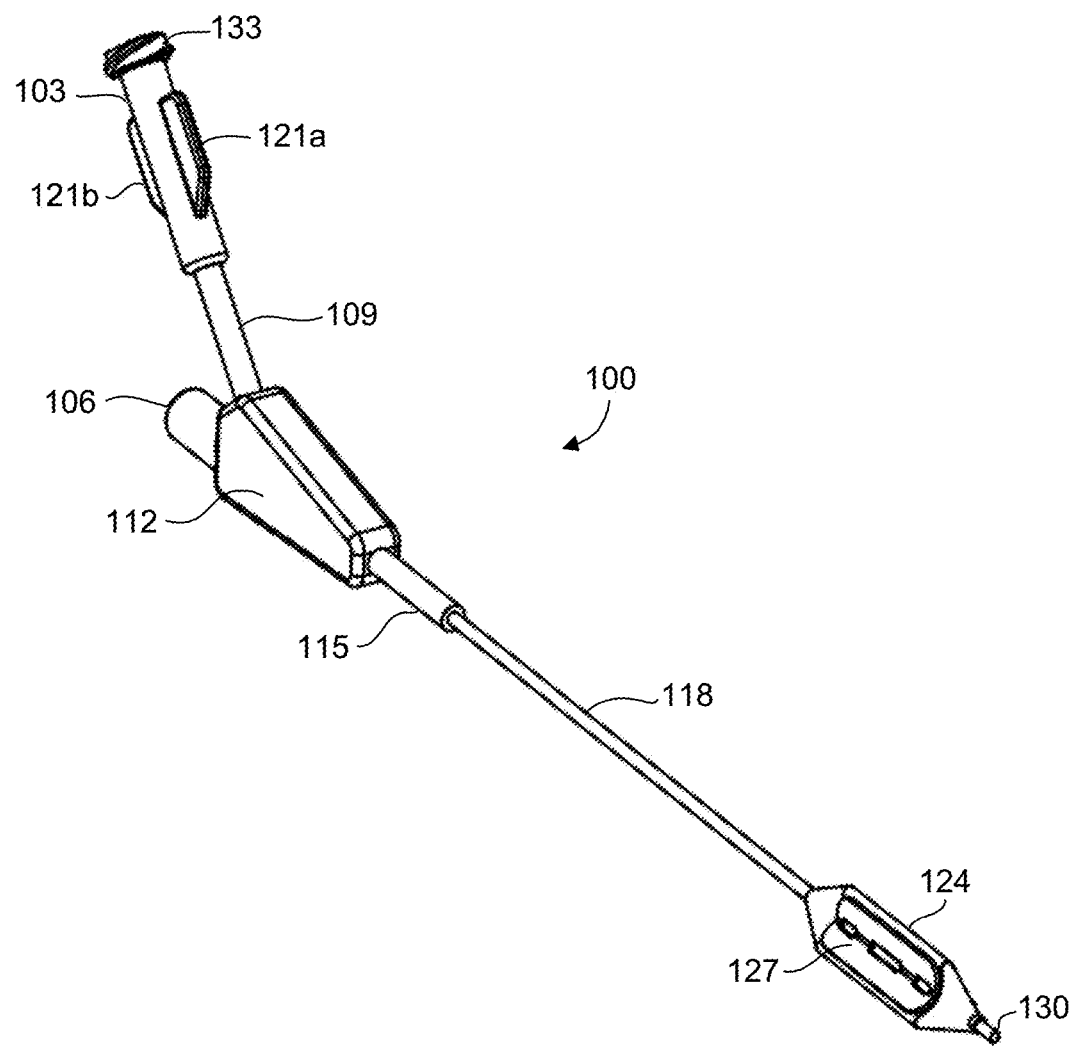
FIG. 2A illustrates a perspective view of the collapsed balloon dilatation catheter according to one embodiment.

FIG. 2A illustrates a preferred embodiment of the apparatus of the present invention, being a balloon dilatation catheter, generally denoted as 100, for the dilatation of a sinus ostium, mobilize the septum, or engage the middle meatus. The balloon dilatation catheter 100 generally comprises a balloon 124, a shaft 118, a shaft supporting member 115, and a hub 112 with an inflation port 109 and a guide port 106. The hub 112 is a generally trapezoidal supporting member that connects the inflation port 109, wire port 106 and the proximal end of the shaft 118. In one aspect, the guide port 106, the shaft 118, the shaft supporting member 115 and the balloon 124 extend concentrically along the same axially extending line. The balloon catheter 100 generally terminates at a distal tip 130 that projects distally and concentrically from the balloon. The balloon 124 is generally attached to the distal end of the shaft 118, whereas the proximal end of the shaft 118 is attached to the hub 112.

In one aspect, the shaft supporting member 115 is an axially elongated annular structure, where one of the two faces that connect its inner and outer peripheral walls is attached to the hub 112. The inner peripheral wall of the shaft supporting member 115 generally contacts a portion of the outer surface of the shaft as a means to provide stuffiness to the shaft 118. In one aspect, the portion of the shaft 118 covered by the supporting member 115 is approximately a fifth of the total length of the shaft 118. The inflation port 109 extends distally from the hub 112 in an angular direction with respect to the guide port 106 as a means of allowing the operator rotate or shift the balloon dilatation catheter 100 for positioning the distal segment of the force-directional catheter 100 into the target structure of the nasal cavity at various angles appropriate to each individual patient and procedure. In one aspect, the inflation port 109 extends distally from the hub forming a 45 degree angle with the guide port 106.

In one aspect, the balloon 124, shaft 118, shaft supporting member 115, and hub are made of plastic and attached together using a fusing process, adhesive, insert molding or laser welding. Materials for the shaft 118 can include, but are not limited to: polyamide, PEBAX (polyether-block-amide), polyethylene, polyurethane, LCP (liquid crystal polymer), PVC (polyvinyl-chloride) and PET (polyether-terephthalate). In one aspect, internal supportive materials of the force-directional catheter 100 may comprise a variety of metals and pseudoelastic alloys, including; stainless steel (300 series), titanium and nickel-titanium alloys (NiTiNOL). Fusion of these dissimilar materials can be accomplished by using coatings or co-extrusions of compatible materials. Balloon 124 materials can include; polyamide, PEBAX, polyurethane and PET. Preferably, the balloon 124 materials incorporate attributes including non-compliance (balloons that inflate to a fixed diameter) or semi-compliance (balloons that inflate to a designated diameter, with limited capability to over expand under higher pressures) and durability (resistance to tearing or puncture when expanded against rigid and irregular surfaces). As will be understood and appreciated, the components of the sections of the balloon dilatation catheter 100 shown in FIG. 2A can be constructed of virtually any dimension or size, and a variety of materials and sizes are possible according to various embodiments of the present disclosure. Generally, however, the balloon 124 is preferable from about 14 mm to 16 mm in length.

In one aspect, the balloon catheter is formed using an inner tube coaxially arranged within an outer tube. The inner tube defines the guide lumen for passage of the guide. Generally, the balloon catheter 100 slides along the guide, which is a rigid or semi-rigid member received through the guide port 106, advanced through the balloon catheter 100 and that can project distally from the distal tip 130. The annular space formed in between the inner and outer tubes defines the inflation lumen which extends from the inflation port 109, through the shaft 118 and into the balloon 124. In one aspect, the inflation lumen may hold a fluid which is used to inflate the balloon 124. In another aspect, two tubes are contained inside of the shaft 118, where one defines the lumen for passage of the guide, and the other defines the inflation lumen. In one aspect, the inflation port 109, the guide port 106 and the shaft 118 are connected in the hub 112. The inflation port 109 is a tube generally bounded by a Luer connector 103, which receives the fluid to inflate the balloon. The Luer connector 103 can be adhesive bonded or insert molded onto the port tubing. The Luer connector 103 can also be made from compatible polymeric materials, including; polyamide, PEBAX, HDPE (high density polyethylene) or rigid PVC. Connector materials more likely to require adhesive bonding include polycarbonate and acrylic. Metal Luer connectors are also common, and that are mechanically locked to the port inflation 109. The Luer connector 103 allows a fluid delivery system to lock into the inflation port 109 of the balloon catheter 100. As will occur to one of ordinary skill in the art, the Luer connector 103 illustrated in FIG. 2A is generally a tube surrounding approximately half of the inflation port 109 and is terminated in an external thread 133. Further, the Luer connector 103 may comprise two generally trapezoidal grips 121 along its outer peripheral surface facing in opposite directions to facilitate the manual attachment of the fluid delivery system. In one aspect, the fluid delivery system is a syringe containing an uncompressible fluid or a pressure-controlled balloon inflation device.

Figure 2B:
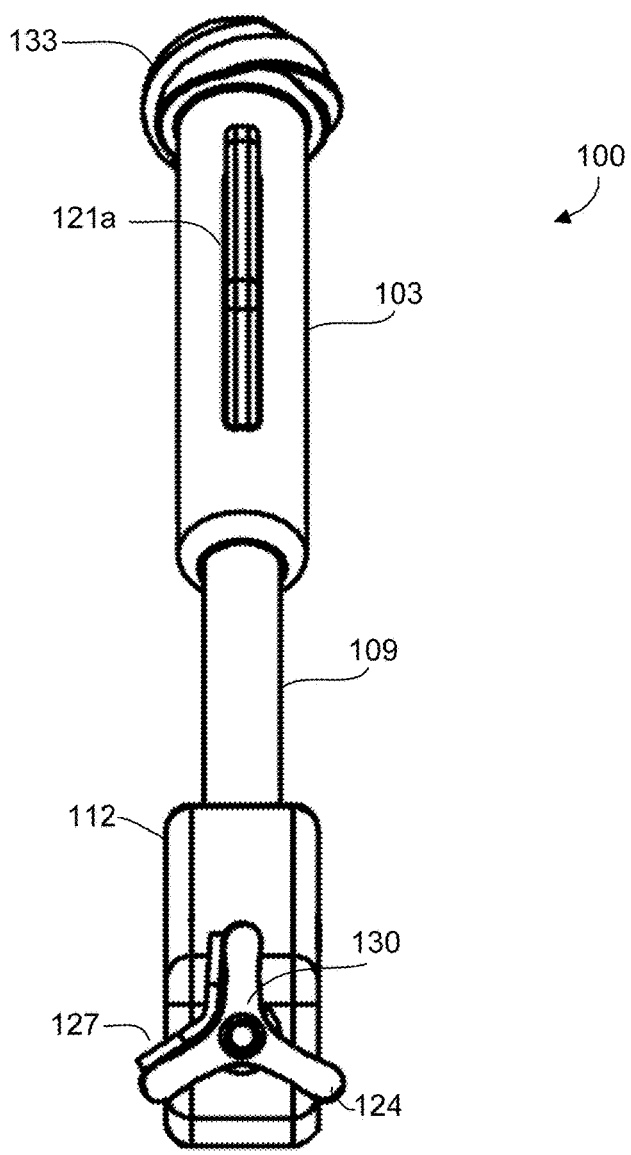
FIG. 2B illustrates a front view of the collapsed balloon dilatation catheter of FIG. 2A.
Figure 2C:
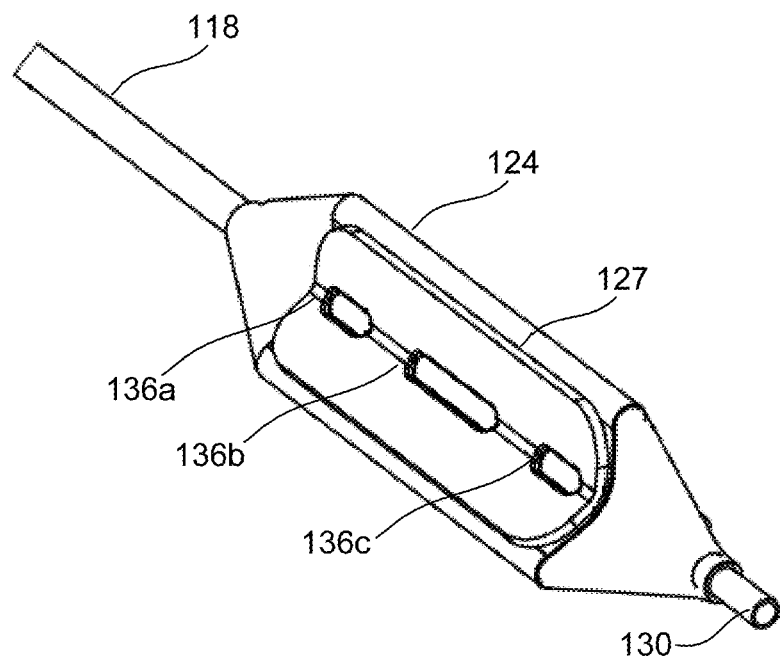
FIG. 2C illustrates a perspective view of the collapsed balloon of FIG. 2A.
Figure 2D:
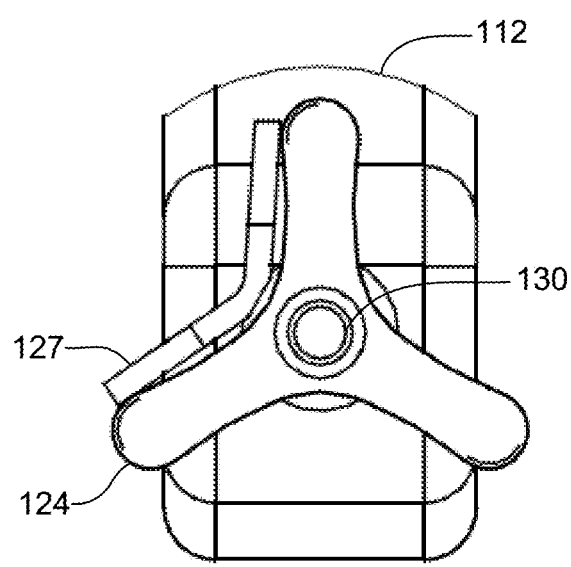
FIG. 2D illustrates a front view of the deflated balloon of FIG. 2A.

Referring to FIG. 2B and FIG. 2D, the collapsed or deflated balloon 124 is a generally folded, star-shaped polygon with three congruent arms that extend distally from the center of the polygon, and are generally positioned 120 degrees from one another. Generally, the folded balloon may have between two and five arms extending from the center, depending on the size of the balloon and the desired folded profile of the deflated balloon. In one aspect, the arms generally form three concentric curved surfaces around the axial line that extends longitudinally through the center of the balloon 124, and a force distribution member 127 is positioned directly over one of the curved surfaces. As illustrated in FIG. 2C, the force distribution member 127 is a generally rectangular flexible member attached to a side of the balloon 124 that adapts to the corresponding shape of the balloon 124. In one aspect, the force distribution member 127 has generally rectangular openings 136 longitudinally distributed along its center to facilitate the bending of the force distribution member 127. In one aspect illustrated in FIG. 2C, the force distribution member 127 has a concentric opening 136b in between two smaller openings 136a, 136c. The openings facilitate the bending of the force distribution member 127 without compromising its structural integrity.

Figure 2E:
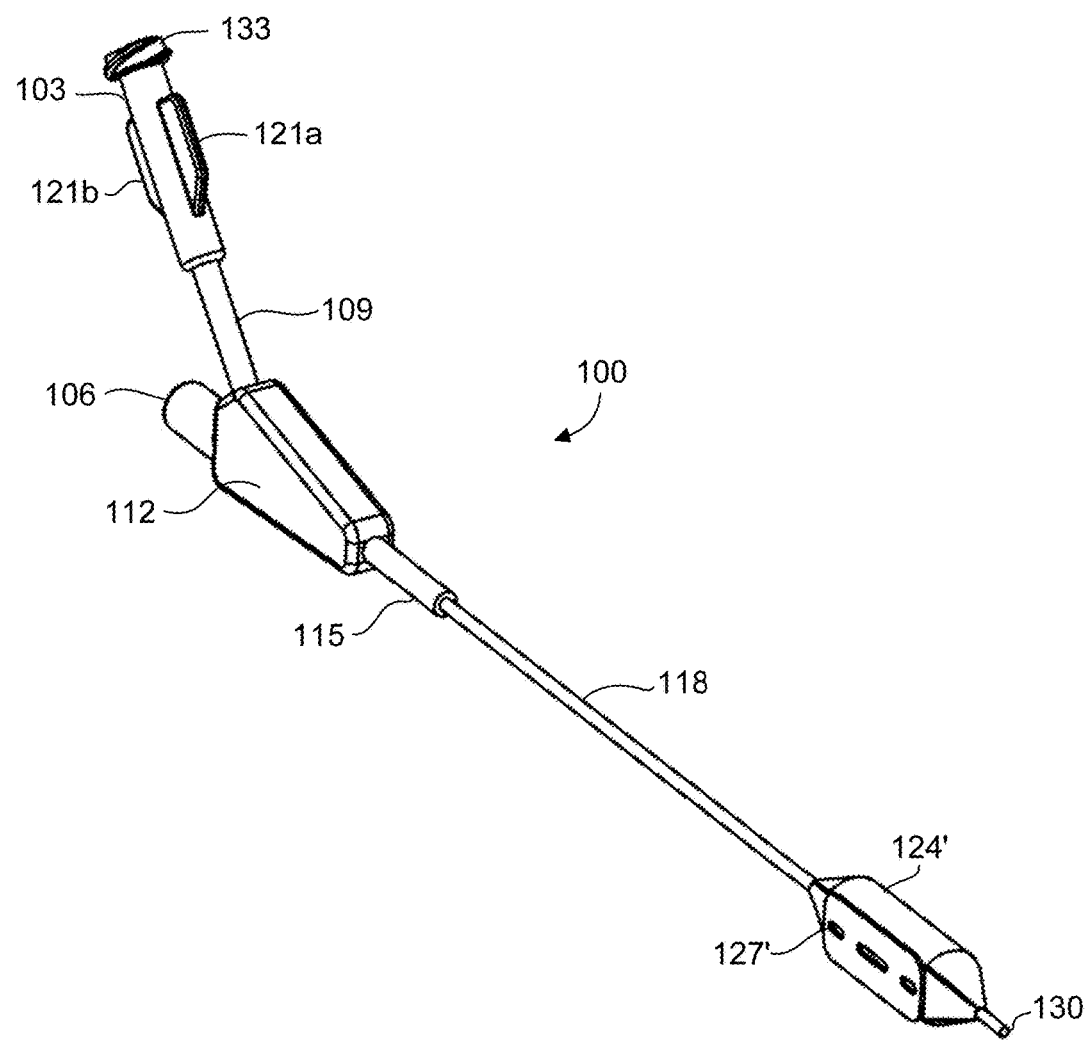
FIG. 2E illustrates a perspective view of the inflated balloon dilatation catheter of FIG. 2A.
Figure 2F:
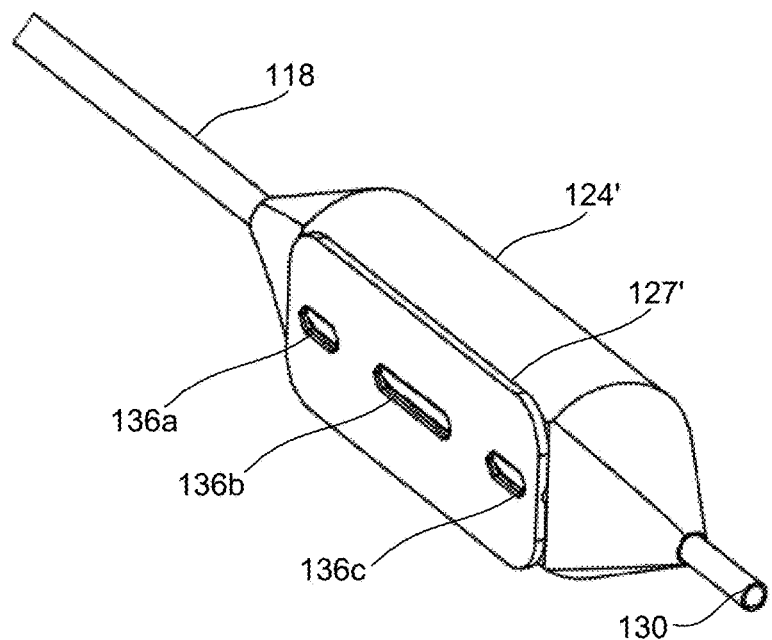
FIG. 2F illustrates a perspective view of the inflated balloon of FIG. 2A.
Figure 2G:
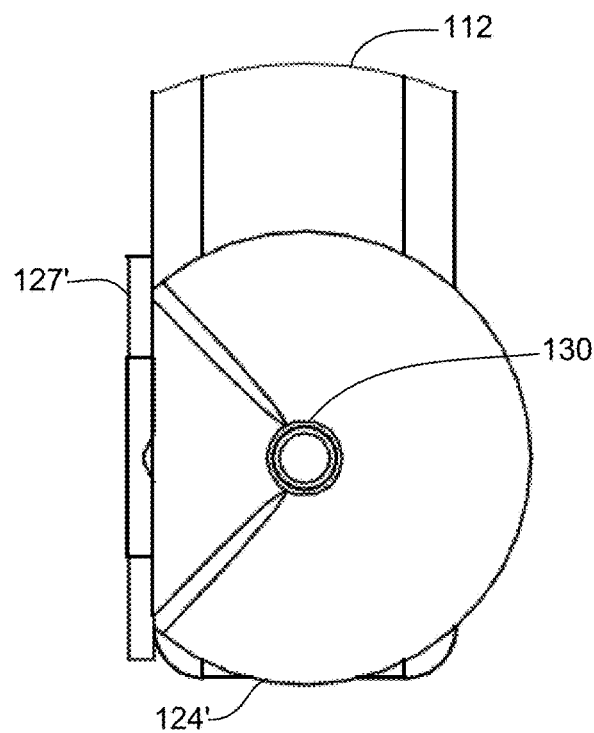
FIG. 2G illustrates a front view of the inflated balloon of FIG. 2A.

As illustrated in FIG. 2E, FIG. 2F and FIG. 2G, the inflated balloon 124' is generally comprised of a flattened planar surface extending axially along a generally cylindrical balloon, as though the cylinder were bisected by a plane passing through two axially extending parallel lines along the outer surface of the cylinder. Generally, the force distribution member 127' is attached to the flattened planar surface of the inflated balloon 124'. The expanded or inflated diameter of the balloon 124' depends on the initial and final desired size of the ostium or nostril to be treated. In one aspect, the balloon 124' inflates to a fixed size and cannot be inflated beyond. In another aspect, the balloon 124' inflates to a maximum size before there is structural damage to the balloon 124', and the pressure applied to the balloon 124' must be regulated with the fluid delivery system or balloon inflation device.

Figure 3A:
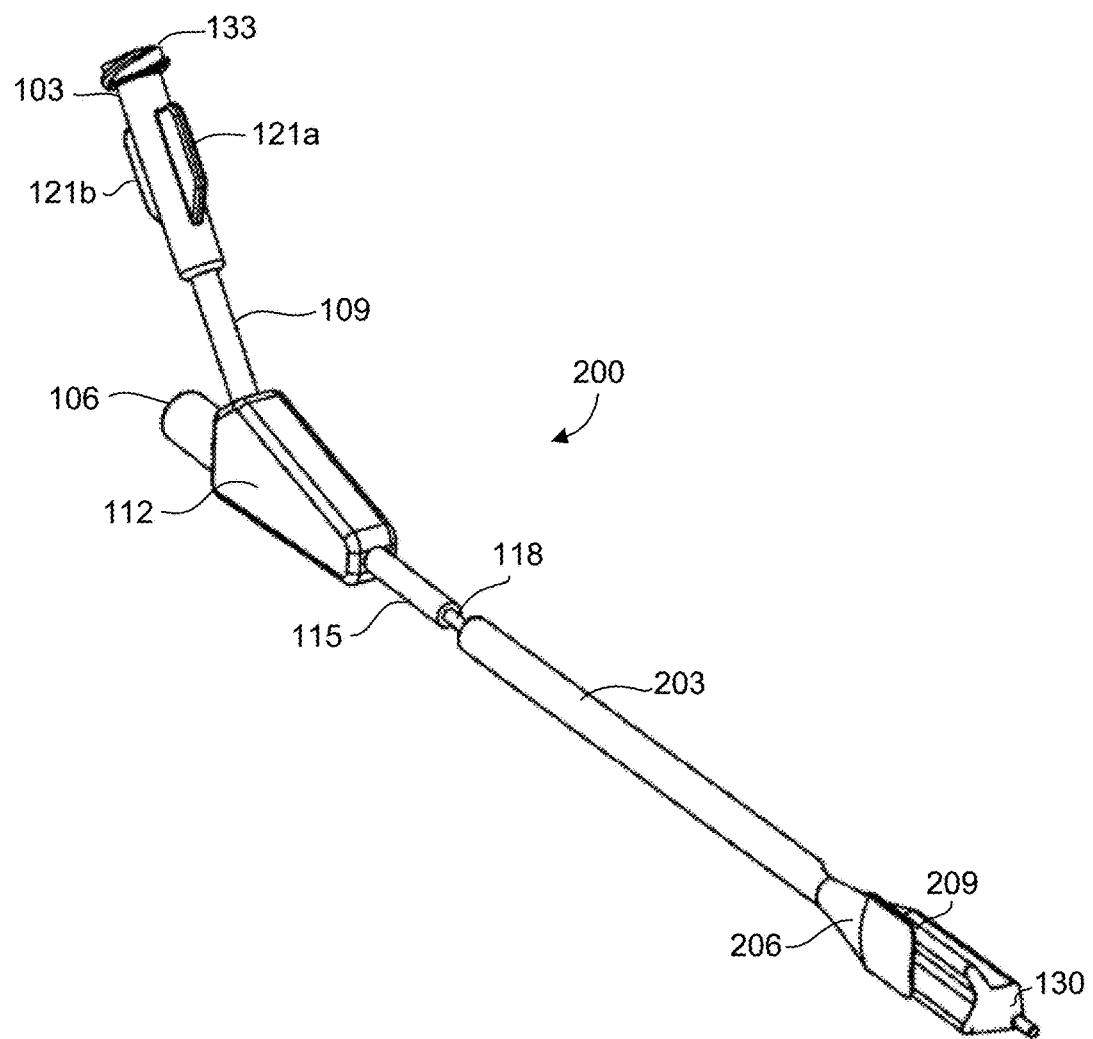
FIG. 3A illustrates a perspective view of the collapsed balloon dilatation catheter according to one embodiment.

Referring now to FIG. 3A, another embodiment of the apparatus of the present invention is illustrated, being a balloon dilatation catheter for the dilatation of a nostril or a sinus ostium, generally denoted as 200. FIG. 3A generally reassembles the embodiment illustrated in FIG. 2A, with a similar balloon 209 and the addition of a force-directional member 206 and a shaft shielding member 203. The guide port 106, the shaft 118, the shaft supporting member 115, and the balloon 124 generally extend concentrically along the same axially extending line. In one aspect, the shaft shielding member 203 is a generally hollow, rigid, cylinder extending concentrically along the same axially extending line as the shaft 118 as though the cylinder were bisected by a plane passing through two axially extending parallel lines along the outer surface of the shaft 118 or two axially extending parallel lines in close proximity to the outer surface of the shaft 118.

In one aspect, the shaft shielding member 203 extends from the distal end of the shaft supporting member 115 to the distal end of the shaft 118. Generally, the shaft shielding member 203 is attached to the shaft 118 as a means to provide sturdiness to the force-directional member 206. In one embodiment, however, the shaft shielding member 203 and the shaft 118 are combined into a single member, where the single member attaches directly to the shaft supporting member 115. The balloon force-directional member 206 is a generally marginally-curved plate resting in close proximity to the outer side of the balloon 209 and attached to the distal end of the shaft shielding member 115. In one aspect, the balloon force-directional member 206 is comprised of two plates attached together and extending parallel to the balloon 209. The first plate of the balloon force-directional member 206 is a generally trapezoidal plate with the parallel side of smaller dimensions attached to the distal end of the shaft shielding member. The second plate of the balloon force-directional member 206 is a generally rectangular plate with one side attached to the distal end of the first plate of the balloon force-directional member 206. In one aspect, the two plates comprised by the balloon force-directional member 206 have approximately the same length, and the balloon force-directional member 206 has a length of approximately half the length of the balloon 209. The balloon 209 is generally attached to the distal end of the shaft 118, whereas the proximal end of the shaft 118 is attached to the hub 112.

In one aspect, the balloon 209, a force-directional member 206, shaft 118, shaft supporting member 115, shaft shielding member 203, and hub 112 are made of plastic and attached together using a fusing process, adhesive, insert molding or laser welding. Balloon 209 materials can include; polyamide, PEBAX, polyurethane and PET. Preferably, the balloon 209 materials incorporate attributes including non-compliance (balloons that inflate to a fixed diameter) or semi-compliance (balloons that inflate to a designated diameter, with limited capability to over expand under higher pressures) and durability (resistance to tearing or puncture when expanded against rigid and irregular surfaces). Materials for the balloon dilatation catheter 200 include, but are not limited to: polyamide, PEBAX (polyether-block-amide), polyethylene, polyurethane, LCP (liquid crystal polymer), PVC (polyvinyl-chloride) and PET (polyether-terephthalate). Internal supportive materials of the balloon dilatation catheter 200 can incorporate a variety of metals and pseudoelastic alloys, including; stainless steel (300 series), titanium and nickel-titanium alloys (NiTiNOL). Generally, fusion of these dissimilar materials can be accomplished by using coatings or co-extrusions of compatible materials. As will be understood and appreciated, the components of the sections of the balloon dilatation catheter 200 shown in FIG. 3A can be constructed of virtually any dimension or size, and a variety of materials and sizes are possible according to various embodiments of the present disclosure. Generally, however, the collapsed balloon 124 is preferable from about 14 mm to 16 mm in length.

Figure 3B:
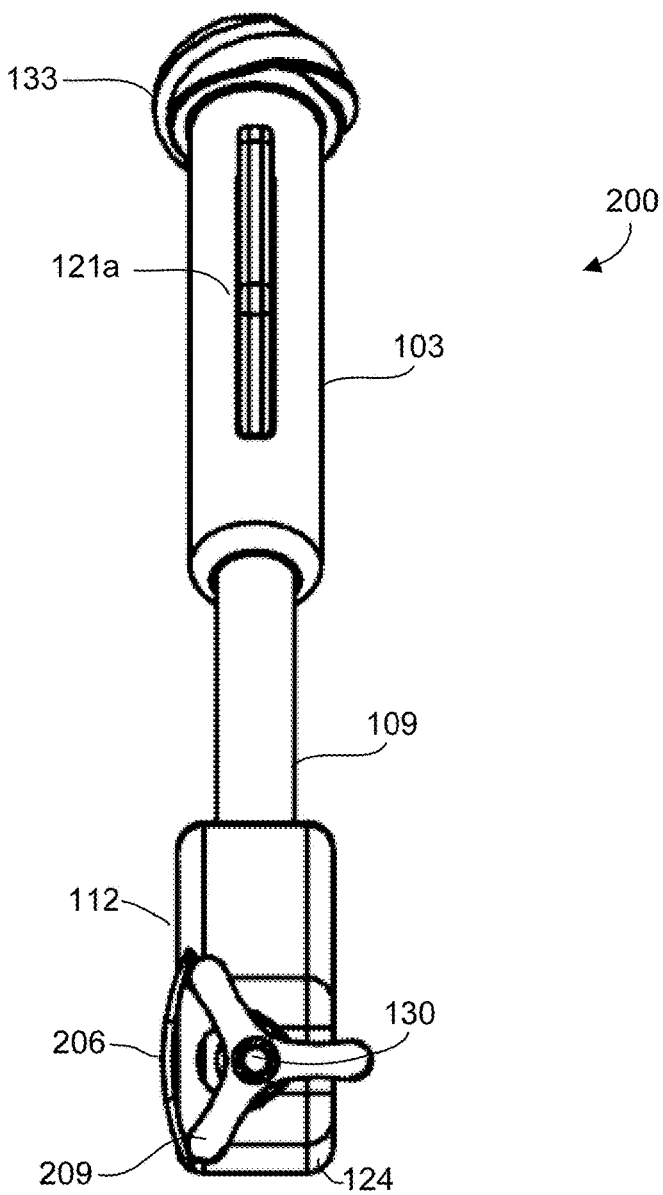
FIG. 3B illustrates a front view of the collapsed balloon dilatation catheter of FIG. 3A.
Figure 3C:
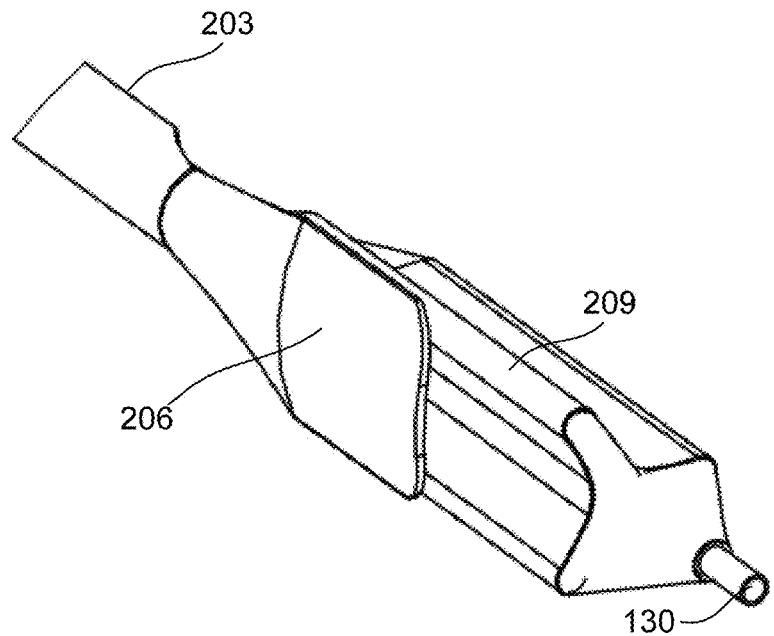
FIG. 3C illustrates a perspective view of the collapsed balloon of FIG. 3A.
Figure 3D:
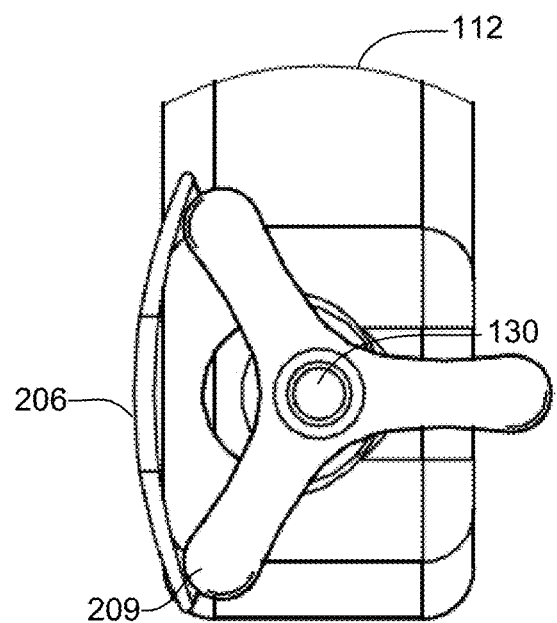
FIG. 3D illustrates a front view of the deflated balloon of FIG. 3A.

Referring to FIG. 3B, FIG. 3C and FIG. 3D, the collapsed or deflated balloon 209 is a folded generally star-shaped polygon with three congruent arms that extend distally from the center of the polygon, and are generally positioned 120 degrees from one another. The folded balloon may have between two and five arms extending from the center, depending on the size of the balloon and the desired folded profile of the deflated balloon 209. The arms generally form three concentric curved surfaces around the axial line that extends longitudinally through the center of the balloon 124. In one aspect, the balloon force-directional member 206 is positioned in close proximity to the balloon 209, and the edges of the balloon force-directional member 206 abut at least one of the arms extending from the center of the balloon 209. In one aspect illustrated in FIG. 3B, FIG. 3C and FIG. 3D, the edges of the balloon force-directional member 206 abut two of the arms extending from the center of the balloon 209.

Figure 3E:
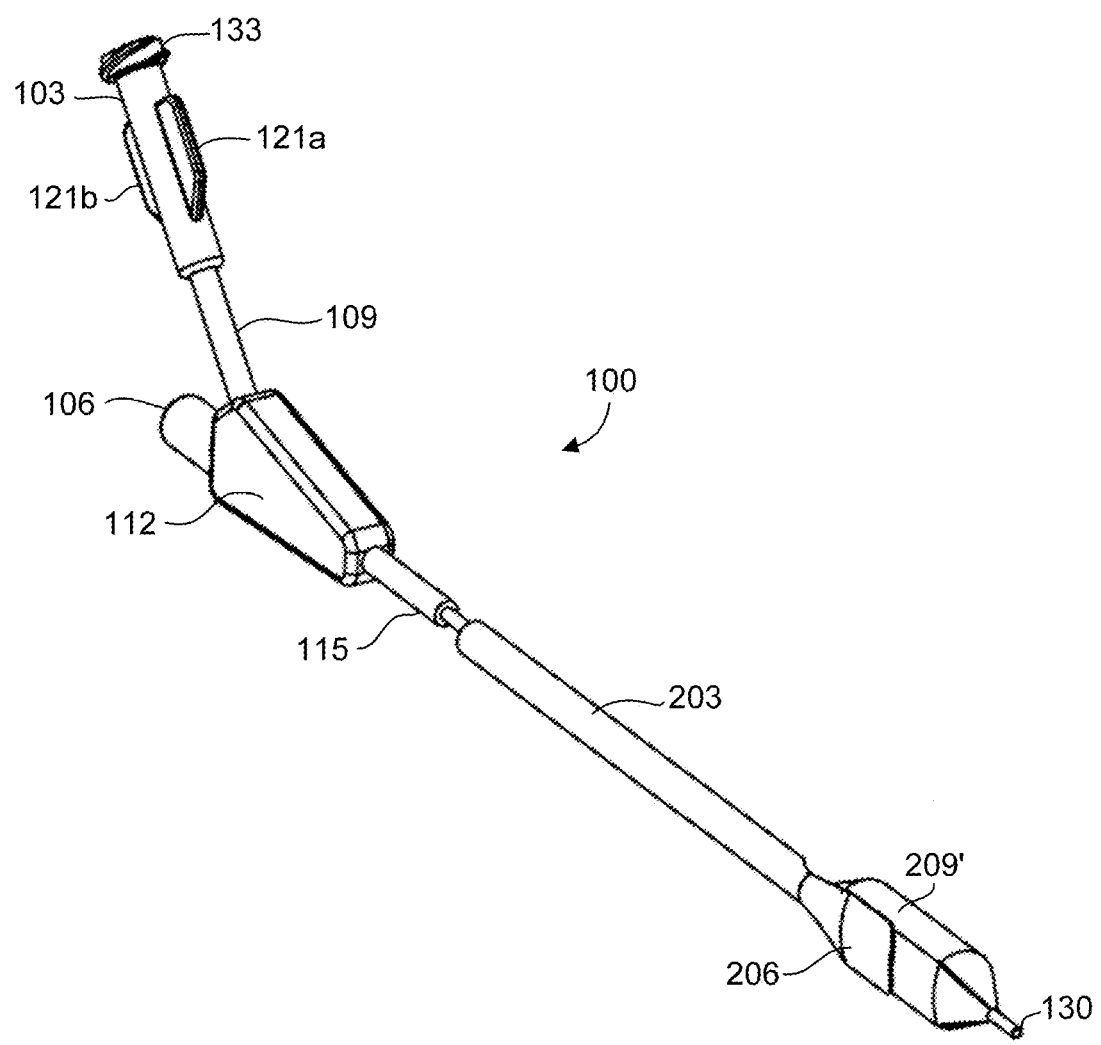
FIG. 3E illustrates a perspective view of the inflated balloon dilatation catheter of FIG. 3A.
Figure 3F:
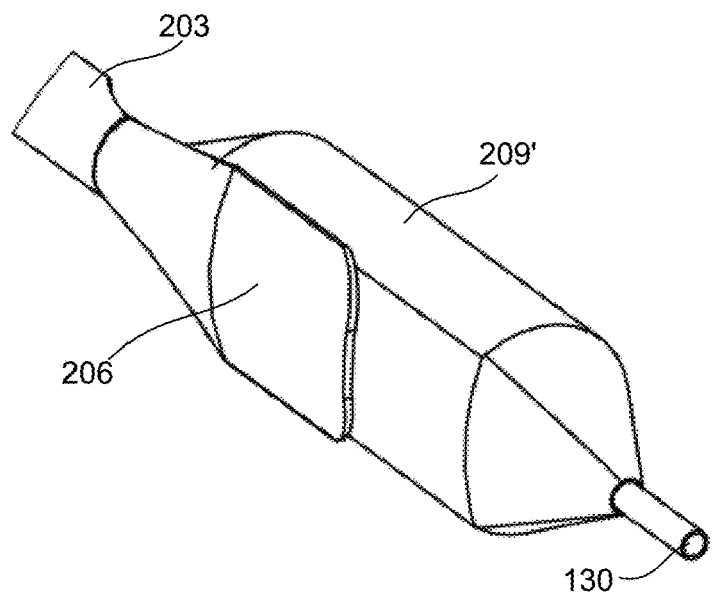
FIG. 3F illustrates a perspective view of the inflated balloon of FIG. 3A.
Figure 3G:
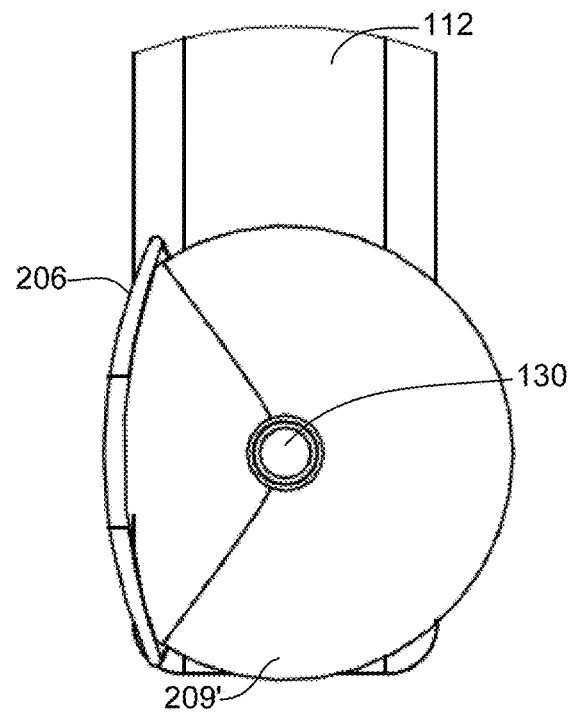
FIG. 3G illustrates a front view of the inflated balloon of FIG. 3A.

As illustrated in FIG. 3E, FIG. 3F and FIG. 3G, the inflated balloon 209' is comprised of a marginally-curved surface extending along a generally cylindrical balloon 209', as though the cylinder were bisected by a plane passing through two axially extending parallel lines along the outer surface of the cylinder, and the flattened side obtained by the bisection were extended outwardly from the balloon 209' to create a marginally-curved surface. Generally, the marginally-curved surface of the inflated balloon 209' abuts the balloon force-directional member 206, and the inflated balloon 209' and the balloon force-directional member 206 possess the same curvature. In one aspect, the length of balloon force-directional member 206 is approximately the diameter of the inflated balloon 209', and the balloon force-directional member 206 completely covers the marginally-curved surface of the inflated balloon 209'. The expanded or inflated diameter of the balloon 209' depends on the initial and final desired size of the ostium or nostril to be treated. In one aspect, the balloon 209' inflates to a fixed size and cannot be inflated beyond. In an alternate aspect, the balloon 209' inflates to a maximum size before there is structural damage to the balloon 209', and the pressure applied to the balloon 209' must be regulated with the fluid delivery system or balloon inflation device.

Figure 4A:
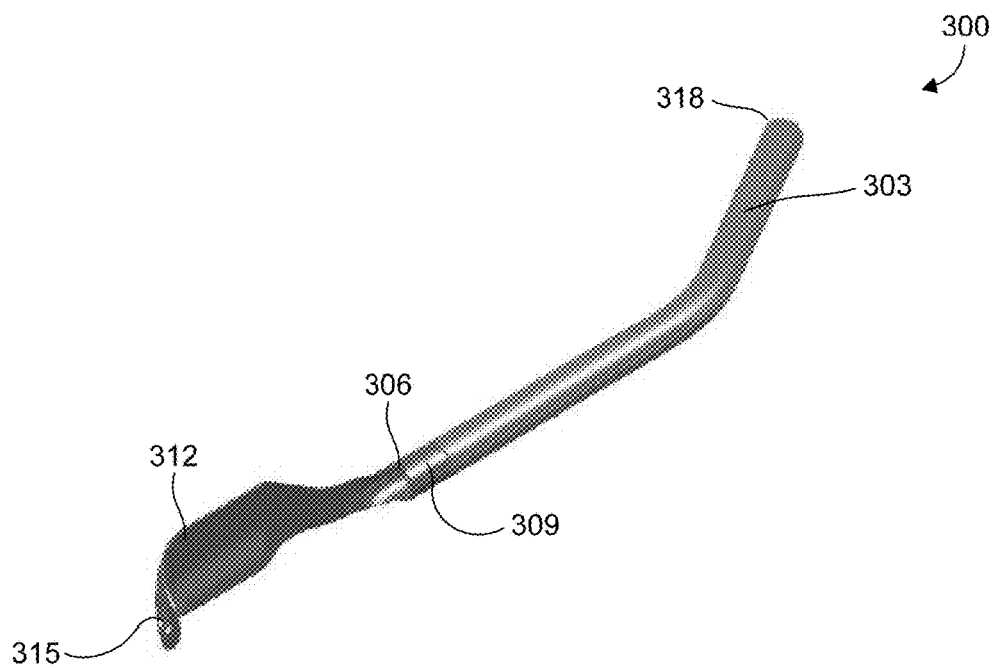
FIG. 4A illustrates a perspective view of the balloon dilatation catheter according to one embodiment.
Figure 4B:
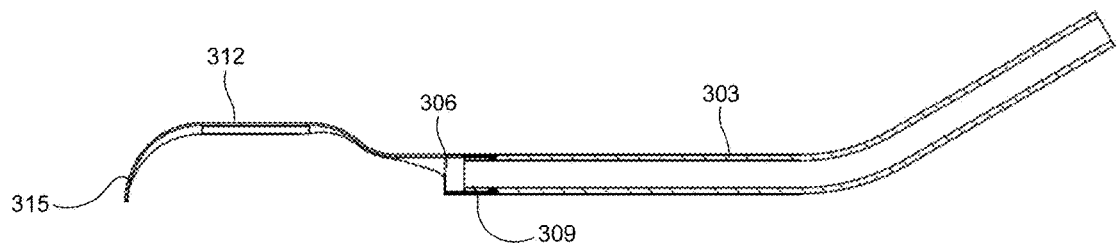
FIG. 4B illustrates a side view of the balloon dilatation catheter of FIG. 4A.
Figure 4C:
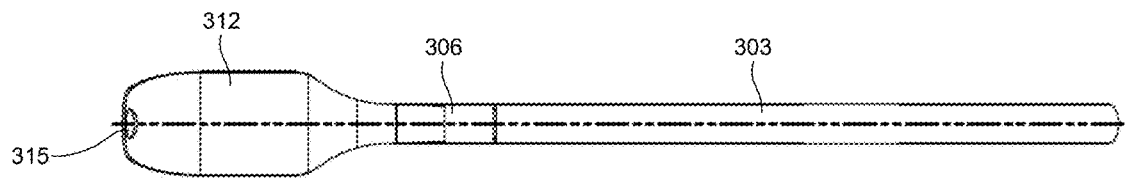
FIG. 4C illustrates a top view of the balloon dilatation catheter of FIG. 4A.

FIG. 4A, FIG. 4B and FIG. 4C illustrate another embodiment of the apparatus of the present invention, generally denoted as 300, being a force-directional device for a balloon dilatation catheter for the dilatation of a sinus ostium, mobilize the septum, or engage the middle meatus. The force-directional device 300 comprises a shaft 303, a connecting system 309, and a force-directional member 312. Generally, the force-directional member 312 is connected to the shaft 303 via the connecting system 309. In one aspect illustrated in FIG. 4B, the force-directional device 300 can be mounted and dismounted from the shaft 303 by the connecting system 309 located at the proximal end of the force-directional member 312. In one aspect, the connecting system 309 is a generally cylindrical member with two adjacent inner annular spaces, where one of the inner annular spaces has a smaller diameter. Generally, the inner annular space of smaller diameter is located furthest from the force-directional member 312, so that the force-directional member 312 can be locked or mounted onto the shaft 303. Generally, the shaft 303 has a cylindrical notch near the distal end of the shaft 303 in accordance with the dimensions of the connecting system 309 as a means to providing a location for the connecting system 309 to lock onto the shaft 303. Generally, the force-directional member 312, the connecting member 309 and the shaft 303 extend along the same axially extending line. In one aspect, the shaft 303 of the force-directional device 300 is bent or angled to provide easier manual operation while accessing the nasal cavity. The shaft 303 is angled at approximately the middle of the shaft 303, but it can be angled at any point as will occur to one of ordinary skill in the art. The angled segment in the shaft 303 allows the operator of the device 300 to rotate or shift the shaft 300 as a means for positioning the distal segment of the force-directional device 300 into the target structure of the nasal cavity at various angles appropriate to each individual patient and procedure.

The force-directional device 300 terminates at a distal aperture 315 located at the distal end of the force-directional device 300. The force-directional member 312 is generally attached to the distal end of the shaft 303, whereas the proximal end of the shaft 118 comprises an aperture or balloon port 318. In one aspect, the shaft 303 in the force-directional device 300 is formed by a generally hollow cylinder, where the inner annular space in the shaft 303 defines the lumen for passage of an object, such as a balloon dilatation catheter. In one aspect, the balloon dilatation catheter is received through the balloon port 318, advanced through the inner annular space formed in the shaft 118, and through the distal opening of the shaft 306 until the tip of the balloon dilatation catheter abuts the force-directional member 312. Generally, the distal tip of the balloon in a balloon dilatation catheter is received through the distal aperture 315 located at the distal end of the force-directional device 300 as a means to fixing the position of the balloon dilatation catheter with respect to the force-directional device 300.

In one aspect, the force-directional member 312, shaft 303, and connecting member 306 are made of plastic and attached together using a fusing process, adhesive, insert molding or laser welding. Materials for the force-directional device 300 include, but are not limited to: polyamide, PEBAX (polyether-block-amide), polyethylene, polyurethane, LCP (liquid crystal polymer), PVC (polyvinyl-chloride) and PET (polyether-terephthalate). Internal supportive materials can incorporate a variety of metals and pseudoelastic alloys, including; stainless steel (300 series), titanium and nickel-titanium alloys (NiTiNOL). Fusion of these dissimilar materials can be accomplished by using coatings or co-extrusions of compatible materials. Balloon materials can include; polyamide, PEBAX, polyurethane and PET. It is preferable that the balloon materials incorporate attributes including non-compliance (balloons that inflate to a fixed diameter) or semi-compliance (balloons that inflate to a designated diameter, with limited capability to over expand under higher pressures) and durability (resistance to tearing or puncture when expanded against rigid and irregular surfaces).

Referring to FIG. 4B and FIG. 4C, the force-directional member 312 is a generally flat plate with a curved distal end to position the distal aperture 315 in a location corresponding with the dimensions of a balloon dilatation catheter, so that after the balloon dilatation catheter has been advanced through the distal opening 306 in the shaft 303, the tip of the balloon dilatation catheter is received through the distal aperture 315 in the force-directional member. Generally, the dimensions of the force-directional member 312 correspond to the dimensions of the inflated balloon of a balloon dilatation catheter. Therefore, when the balloon dilatation catheter has been advanced through the distal opening 306 in the shaft 303, the tip of the balloon dilatation catheter has been received through the distal aperture 315 in the force-directional member, and the balloon in the balloon dilatation catheter has been inflated, the force-directional member constrains the expansion of the balloon beyond the contour of the force-directional member 312. In one aspect, the force-directional member 312 is a generally rectangular member attached to a side of the balloon 124, which adapts to the corresponding shape of the force-directional member 312.

FIGS. 5A-5D and 6A-6D illustrate use of a balloon dilatation catheter device 100 in connection with a nasal surgery.

Figure 5A:
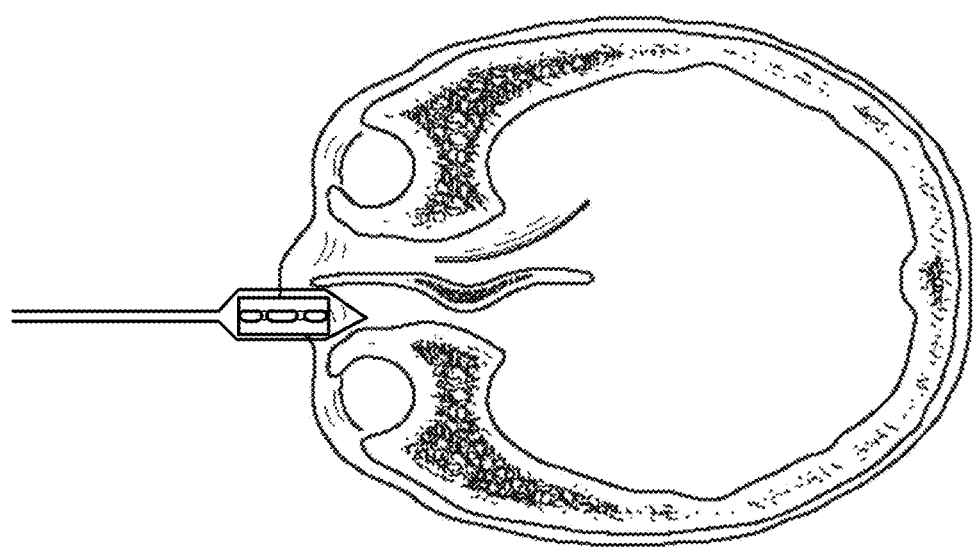
FIG. 5A is an axial cross-sectional view of a human skull through a region involving the nasal passages, illustrating the insertion of an exemplary collapsed balloon dilatation catheter for a deviated septum procedure.

FIG. 5A is an axial cross-sectional view of a human skull through a region involving the nasal passages, illustrating the insertion of an exemplary collapsed balloon dilatation catheter 100 for a deviated septum procedure.

Figure 5B:
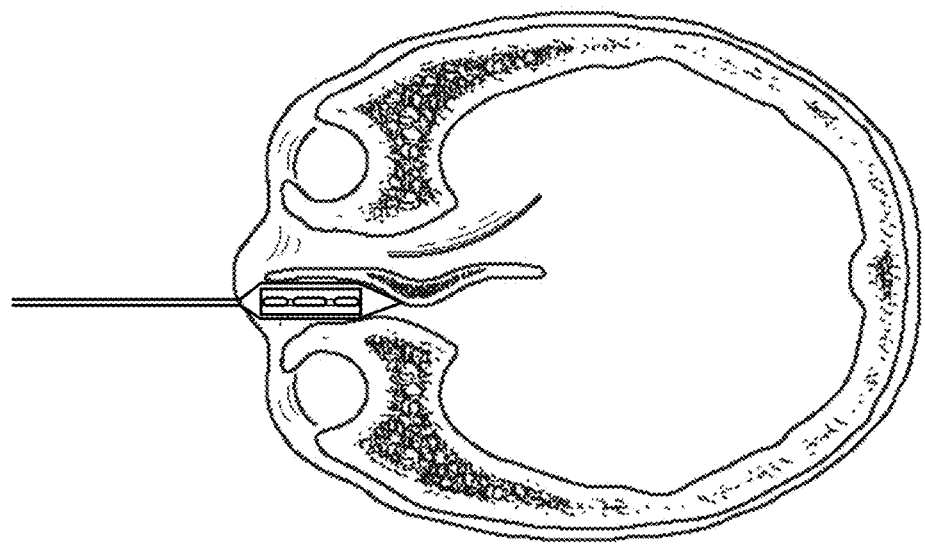
FIG. 5B is an axial cross-sectional view of a human skull through a region involving the nasal passages, illustrating the placement of an exemplary collapsed balloon dilatation catheter into position prior to inflation for a deviated septum procedure.

FIG. 5B is an axial cross-sectional view of a human skull through a region involving the nasal passages, illustrating the placement of an exemplary collapsed balloon dilatation catheter 100 into position prior to inflation for a deviated septum procedure.

Figure 5C:
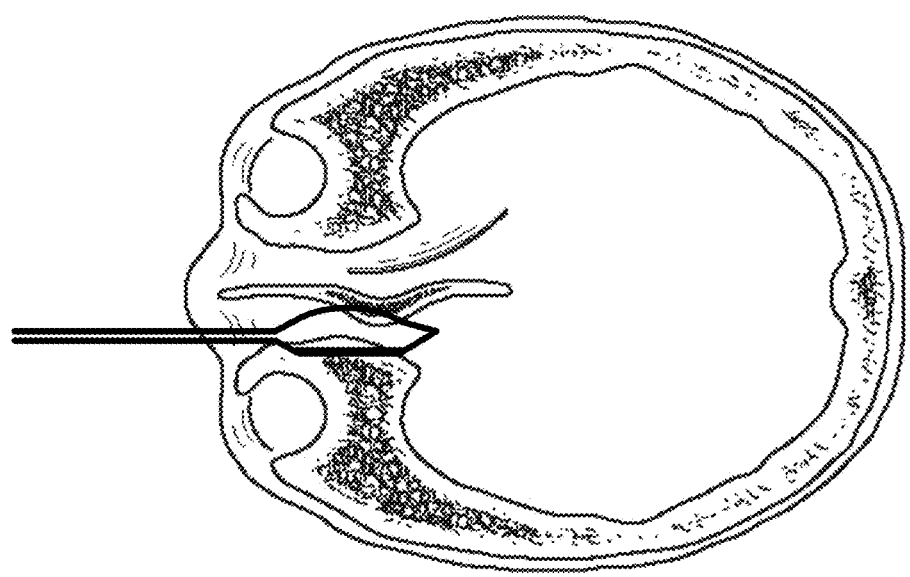
FIG. 5C is an axial cross-sectional view of a human skull through a region involving the nasal passages, illustrating the inflation of an exemplary balloon dilatation catheter for a deviated septum procedure.

FIG. 5C is an axial cross-sectional view of a human skull through a region involving the nasal passages, illustrating the inflation of an exemplary balloon dilatation catheter 100 for a deviated septum procedure.

Figure 5D:
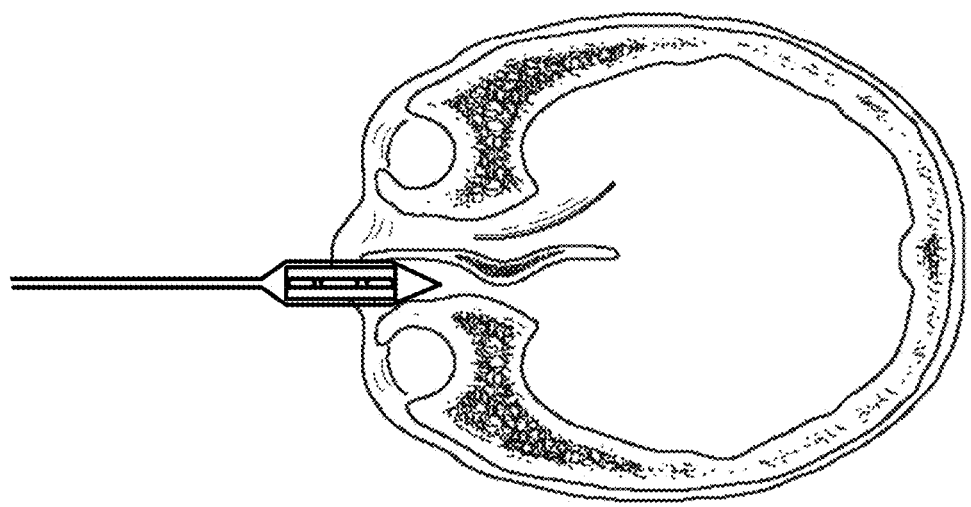
FIG. 5D is an axial cross-sectional view of a human skull through a region involving the nasal passages, illustrating the deflation of an exemplary balloon dilatation catheter and removal (or repositioning) of the device after a deviated septum procedure.

FIG. 5D is an axial cross-sectional view of a human skull through a region involving the nasal passages, illustrating the deflation of an exemplary balloon dilatation catheter 100 and removal (or repositioning) of the device after a deviated septum procedure. As will be appreciated, the balloon of the device may be deflated, and the device repositioned for subsequent inflation against a different surface, or repeatedly against the same surface, until the desired results are achieved, prior to deflating the balloon and removing the device.

Figure 6A:
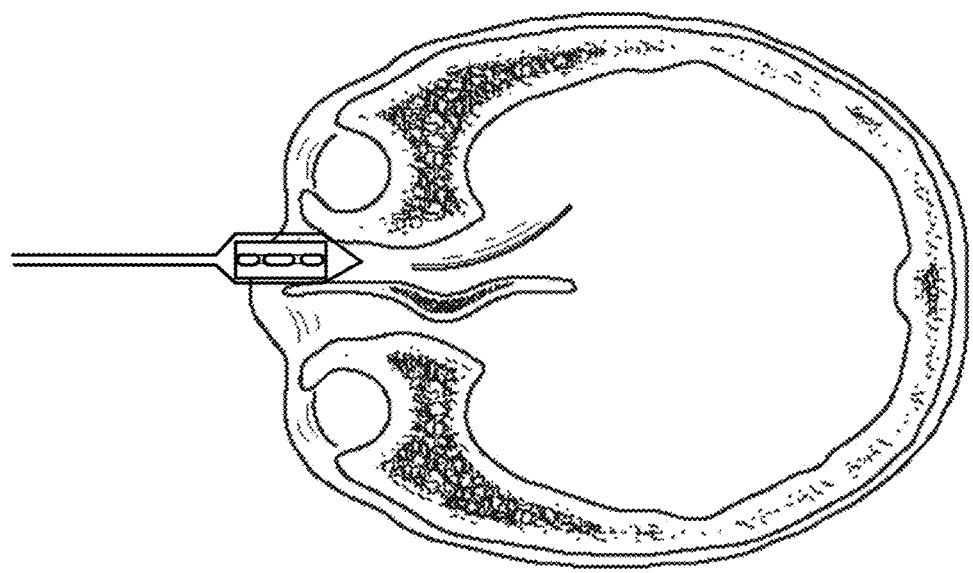
FIG. 6A is an axial cross-sectional view of a human skull through a region involving the nasal passages, illustrating the insertion of an exemplary collapsed balloon dilatation catheter for a procedure involving the middle turbinate.

FIG. 6A is an axial cross-sectional view of a human skull through a region involving the nasal passages, illustrating the insertion of an exemplary collapsed balloon dilatation catheter for a procedure involving the middle turbinate.

Figure 6B:
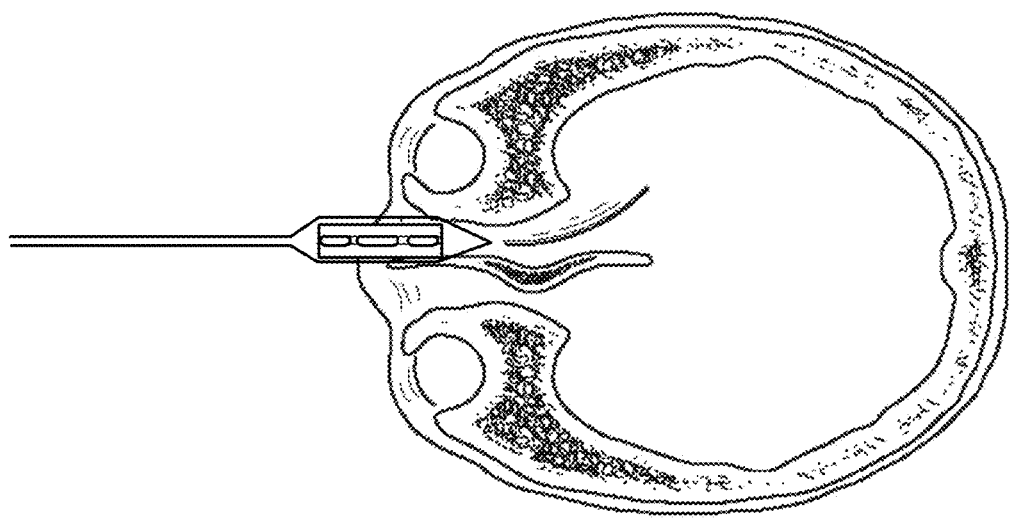
FIG. 6B is an axial cross-sectional view of a human skull through a region involving the nasal passages, illustrating the placement of an exemplary collapsed balloon dilatation catheter for a procedure involving the middle turbinate.

FIG. 6B is an axial cross-sectional view of a human skull through a region involving the nasal passages, illustrating the placement of an exemplary collapsed balloon dilatation catheter for a procedure involving the middle turbinate.

Figure 6C:
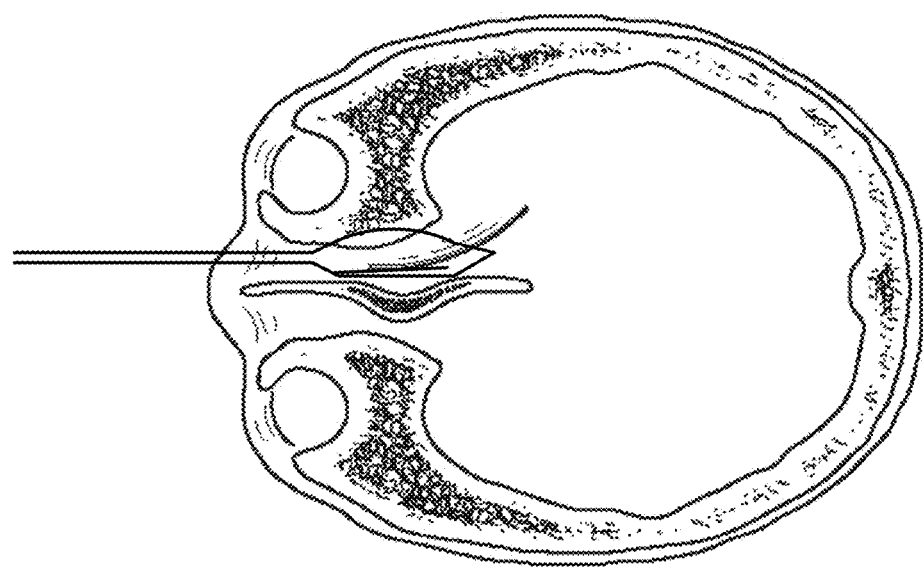
FIG. 6C is an axial cross-sectional view of a human skull through a region involving the nasal passages, illustrating the inflation of an exemplary balloon dilatation catheter for a procedure involving the middle turbinate.

FIG. 6C is an axial cross-sectional view of a human skull through a region involving the nasal passages, illustrating the inflation of an exemplary balloon dilatation catheter for a procedure involving the middle turbinate.

Figure 6D:
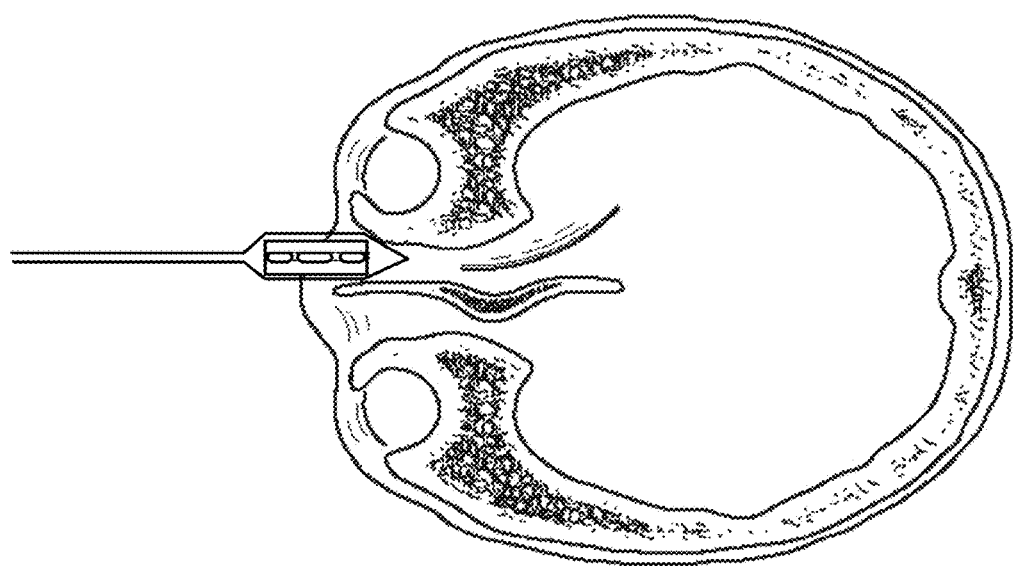
FIG. 6D is an axial cross-sectional view of a human skull through a region involving the nasal passages, illustrating the deflation of an exemplary balloon dilatation catheter and removal of the device (or repositioning) after a procedure involving the middle turbinate.

FIG. 6D is an axial cross-sectional view of a human skull through a region involving the nasal passages, illustrating the deflation of an exemplary balloon dilatation catheter and removal of the device (or repositioning) after a procedure involving the middle turbinate. As will be appreciated, the balloon of the device may be deflated, and the device repositioned for subsequent inflation against a different surface, or repeatedly against the same surface, until the desired results are achieved, prior to deflating the balloon and removing the device.

During a medical procedure to treat the nasal cavity illustrated in FIGS. 5A-5D and 6A-6D, the operator (e.g. surgeon) generally holds an elongated, tubular, at least semi-rigid guide 406 in one hand using a handler or similar member. In some aspects, the guide is coupled to an endoscope for visual recognition of the nasal cavity 412. Generally, a balloon dilatation catheter resides within the lumen of the guide 406, and the distal end of the guide 406 is advanced through the nostril 415 to a position in proximity to the opening 415 of a paranasal sinus 400 (i.e. sinus ostium) with the aid of the endoscopic visualization. In some cases, the guide has a light source at the distal end for viewing the emitted light from the outside of the patient to confirm that the guide is located in the target position. Once the target position of the guide 406 has been reached and confirmed, the balloon dilatation catheter is generally advanced through the guide 406 to position the balloon dilatation catheter in the opening of a sinus ostium 415. In one aspect, a flexible wire 403 is introduced through the inner guide 406 and gently advanced into the target sinus 418. The balloon dilatation catheter generally slides through the inner guide 406 and over the flexible wire 403, and it is positioned across the constricted ostium 415. The balloon dilatation catheter is then expanded to apply an omnidirectional force that dilates the opening 415 of the paranasal sinus 418. The balloon catheter dilatation remodels both the sinus ostium 415 tissues and bone adjacent to the sinus ostium 415, without invasive procedures such as incisions of the mucosa or removal of any bone. The balloon dilatation catheter and guide are then removed and the dilated sinus ostium 415 allows for improved drainage from and ventilation of the paranasal sinus 418. Depending on the patient and physical differences in the nasal cavity from patient to patient, a conventional Balloon Sinuplasty™ may be challenging or impossible. The paranasal sinuses 418 lie between the upper parts of the nasal cavities and the eye orbits, and are separated from these cavities by delicate, thin bony laminae. In that location, the paranasal sinuses 418 are in close proximity to delicate structures such as the optic nerve, extraocular muscles that move the eyes, the eye orbits, brain, meninges, and nasolacrimal duct. Due to the complex and delicate anatomy of the aforementioned structures and differences from patient to patient, a balloon dilatation catheter that applies omnidirectional force on the surrounding structure during a procedure has the potential of causing damage to the delicate structures surrounding the paranasal sinuses.

In order to protect the delicate structures surrounding the paranasal sinuses, the devices 100, 200, 300 of the present disclosure can be utilized. For example, the balloon dilatation catheter 100 illustrated in FIG. 2A and FIGS. 5A-5D and 6A-6D can be advanced through the guide 406 and over the flexible wire 403 to the opening 415 of the target sinus 418. As the balloon 124' is inflated, the force distribution member 127' generally shields the delicate structures, or the structures surrounding a delicate structure by directing the force applied by the dilatation of the balloon 124' towards other directions as illustrated in FIG. 2F and FIG. 2G.

Generally, as determined empirically when the balloon 124' is inflated, the external surface of the balloon 124' parallel and opposite to the force distribution member 127' is approximately one third of the size of the external side surface of the force distribution member 127'. Similarly, the balloon dilatation catheter 200 illustrated in FIG. 2A may be advanced through the guide 406 and over the flexible wire 403 to the opening 415 of the target sinus 418. As the balloon 209' is inflated, the force-directional member 206 generally shields the delicate structures, or the structures surrounding a delicate structure by directing the force applied by the dilatation of the balloon 124' towards other directions as illustrated in FIG. 3F and FIG. 3G.

Generally, when the balloon 209' is inflated, both the force-directional member 206 and the external surface of the balloon 209' parallel and opposite to the force-directional member 206 apply pressure on a section of tissue or physical structure in the nasal cavity 412. Preferably, the area of the balloon 209' that applies pressure to a physical structure is approximately a third of the area of the force-directional member 206 that applies pressure to a physical structure in the nasal cavity 412. Finally, the force-directional device 300 illustrated in FIG. 4A can be used with traditional balloon dilatation catheters used in a sinuplasty procedure, where a traditional balloon is advanced through the shaft 303 and mounted on the force-directional member 312. In one aspect, both the balloon dilatation catheter and the force-directional device 300 can be advanced through the guide 406 and over the flexible wire 403 to a target opening 415 of a sinus 418. As the balloon is inflated, the force-directional member 312 directs the force applied by the dilatation of the balloon away from the delicate structures.

Figure 7:
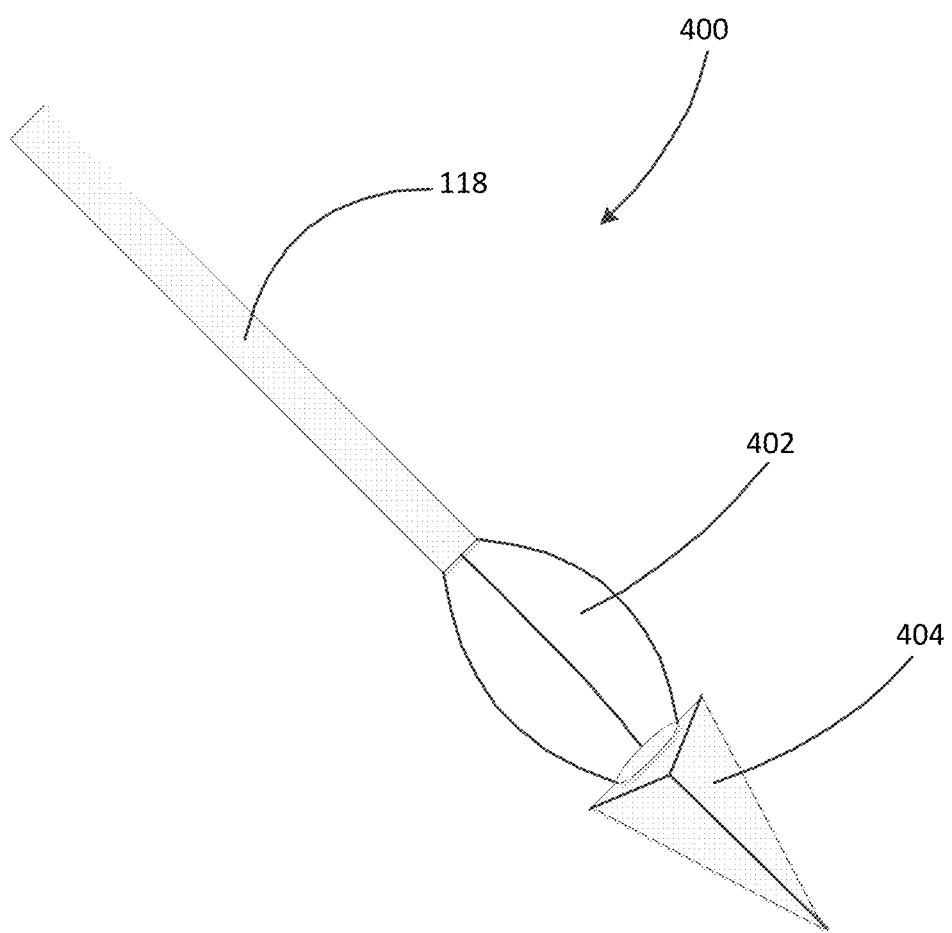
FIG. 7 is a schematic of a balloon dilatation device comprising a wedge which is driven forward upon inflation of the balloon.

FIG. 7 is a schematic of a balloon dilatation device comprising a wedge which is driven forward upon inflation of the balloon. As shown in FIG. 7, the balloon dilatation catheter 400 comprises a balloon 402 located at the distal end of a shaft 118. As shown in FIG. 7, a force application member 404 is positioned at the distal end of the balloon 402. Balloon 404 expands laterally (i.e., in the proximal-distal direction with respect to the shaft) upon inflation. Upon inflation of the balloon, force application member 404 is driven forward, away from the shaft 118. As shown in FIG. 7, force application member 404 can have a wedge shape wherein the thickness of the member increases in the distal to proximal direction. In use, force application member 404 is positioned anterior of the area to be treated such that, upon inflation, force application member 404 is driven forward relative to shaft 118 and into a position adjacent the area to be treated. As shown in FIG. 7, force application member 404 is attached to the distal end of balloon 404. Force application member 404, however, can also be movably attached to shaft 118 forward of the balloon in such a manner as to allow axial separation from the shaft.

Figure 8:
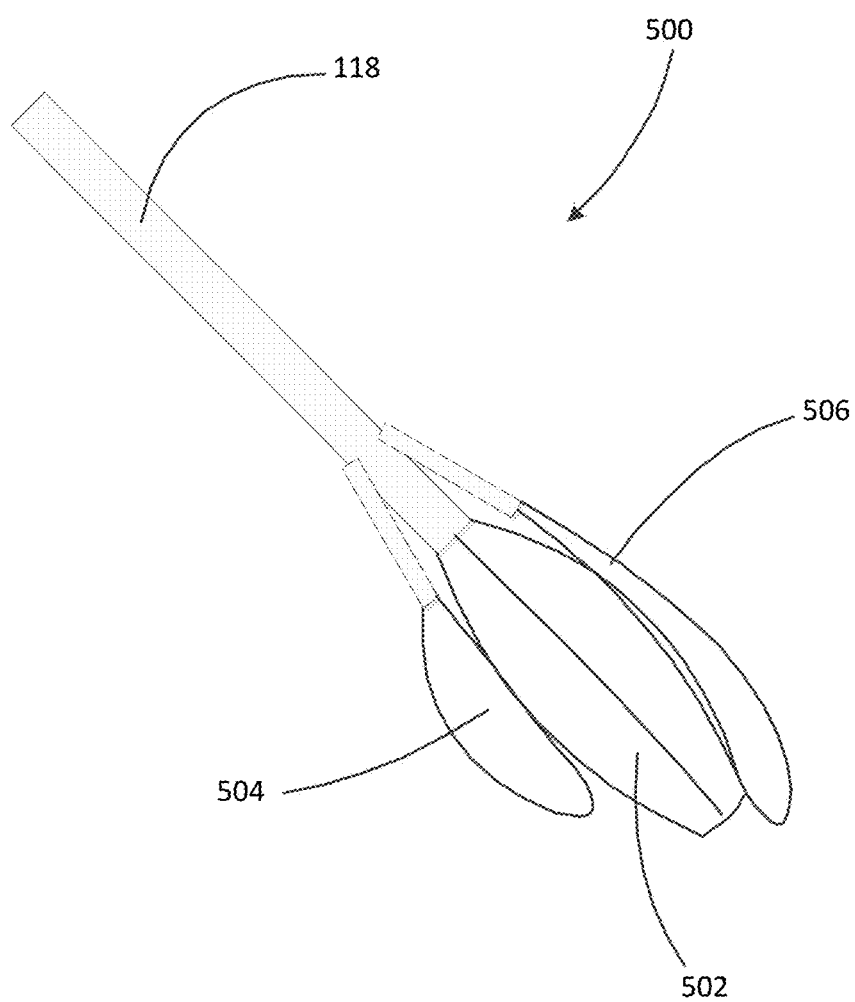
FIG. 8 is a schematic of a balloon dilatation device comprising first and second wedge elements which are forced apart by the inflation of the balloon.

FIG. 8 is a schematic of a balloon dilatation device comprising first and second wedge elements which are forced apart by the inflation of the balloon. As shown in FIG. 8, balloon dilatation catheter 500 comprises a balloon 502 located at the distal end of a shaft 118. The device also includes first and second wedge elements 504 and 506. As shown in FIG. 8, first and second wedge elements 504 and 506 are movably attached to shaft 118 to allow separation upon inflation of balloon 502. As also shown in FIG. 8, both wedge elements have an outer convex surface. However, first wedge element 504 has a greater degree of curvature than second wedge element 506. Accordingly, upon inflation of balloon 502, first wedge element 504 will apply greater pressure to adjacent tissue than second wedge element 506. In use, second wedge element 506 can be positioned adjacent anatomical structures susceptible to damage in order to reduce the pressure applied to such structures during treatment. While first and second wedge elements having curved outer surfaces are shown in FIG. 8, these surfaces may be flat or have other shapes.

In certain patients with certain nasal anatomy or in in complex anatomical situations, such as irregularities in the nasal cavity 412, the devices described herein can be used to modify the anatomy of the nasal cavity 412 either momentarily or permanently. In one aspect, the modification of the anatomy of the nasal cavity by the devices described herein can allow easier manipulation of medical instruments inside of the nasal cavity 412 during medical procedures, such as sinuplasty and septoplasty. During a septoplasty procedure, for example, the devices as described herein can be used to hold the necessary space open in the nasal cavity 412, and the flattened surface of the devices 100, 200, 300 aid in creating a flattened surface nearby that improves the working surface for conducting the septoplasty tissue removal.

The foregoing description of the exemplary embodiments has been presented only for the purposes of illustration and description and is not intended to be exhaustive or to limit the inventions to the precise forms disclosed. Many modifications and variations are possible in light of the above teaching.

The embodiments were chosen and described in order to explain the principles of the disclosure and their practical application so as to enable others skilled in the art to utilize the inventions and various embodiments and with various modifications as are suited to the particular use contemplated. Alternative embodiments will become apparent to those skilled in the art to which the present disclosure pertain without departing from their spirit and scope.

What is claimed is:

1. A force-directional nasal surgery dilatation device for use in a nasal surgery, comprising:
   an inflatable balloon;
   a shaft for supporting the balloon at a distal end and guiding the balloon into position for a procedure involving a patient;
   an inflation passageway associated with the shaft for introducing an inflation medium into the balloon; and
   a force distribution member adjacent a side of the balloon and having a relatively rigid force distribution surface, said force distribution surface comprising a pair of surfaces that articulate along a line between adjacent lateral edges of the pair of surfaces and allow articulated movement of the pair of surfaces relative to each other when the balloon is inflated; wherein the line between adjacent lateral edges of the pair of surfaces is defined by openings longitudinally distributed along a center to facilitate the bending of the force distribution member; and
   wherein, when the balloon is inflated in a nasal passage or sinus ostia of the patient, the pair of surfaces move relative to each other to provide a force distribution surface such that the force applied to tissue adjacent the force distribution member resulting from inflation of the balloon is distributed along the force distribution surface of the force distribution member and is less than the amount of force applied to other tissue in the nasal passage or sinus ostia of the patient by the inflation of the balloon.

2. The device of claim 1, wherein the openings comprises a first concentric opening positioned in between two smaller openings.

3. The device of claim 1, wherein the inflated balloon is elongate and wherein a portion of the inflated balloon adjacent the force distribution member has a first radius of curvature in cross-section and a portion of the balloon not adjacent the force distribution member has a second radius of curvature in cross-section, wherein the second radius of curvature is smaller than the first radius of curvature.

4. The device of claim 1, wherein the cross-section of the inflatable balloon is multilobal in shape.

5. The device of claim 1, wherein the force distribution member is affixed to the side of the inflatable balloon.

6. The device of claim 1, wherein the line between adjacent lateral edges of the pair of surfaces comprises a hinge between the pair of surfaces.

7. The device of claim 1, wherein the force distribution member is affixed to the distal end of the shaft adjacent to the inflatable balloon.

8. The device of claim 7, wherein the force distribution member is curved.

9. The device of claim 7, wherein the balloon extends distally beyond the endpoint of the force distribution member.

\* \* \* \* \*